United States Patent [19]

Piejko et al.

[11] Patent Number: 4,780,411
[45] Date of Patent: Oct. 25, 1988

[54] WATER-ABSORBING, ESSENTIALLY WATER-FREE MEMBRANE FOR REAGENT SUBSTRATES AND METHODS OF PREPARING THE SAME

[75] Inventors: Karl-Erwin Piejko, Cologne; Bruno Bömer, Bergisch-Gladbach; Herbert Bartl, Odenthal, all of Fed. Rep. of Germany; Georg Frank, Elkhart, Ind.

[73] Assignee: Bayer Aktiengesellschaft, Leverkusen, Fed. Rep. of Germany

[21] Appl. No.: 774,633

[22] Filed: Sep. 11, 1985

[30] Foreign Application Priority Data

Sep. 22, 1984 [DE] Fed. Rep. of Germany ........ 3434822

[51] Int. Cl.[4] .................... G01N 21/77; B05D 3/02; B32B 5/16
[52] U.S. Cl. ........................... 422/56; 422/57; 427/384; 428/327; 435/805; 436/169
[58] Field of Search ............... 422/56, 57, 58; 436/169, 170, 810; 435/805; 427/384; 428/212, 327

[56] References Cited

U.S. PATENT DOCUMENTS

| | | |
|---|---|---|
| 3,092,463 | 6/1963 | Adams, Jr. et al. . |
| 3,092,465 | 6/1963 | Adams, Jr. et al. . |
| 3,630,957 | 12/1971 | Rey et al. . |
| 3,992,158 | 11/1976 | Przybylowicz et al. . |
| 3,993,451 | 11/1976 | Verbeck . |
| 4,042,335 | 8/1977 | Clement . |
| 4,089,747 | 5/1978 | Bruschi . |
| 4,303,408 | 12/1981 | Kim et al. . |
| 4,312,834 | 1/1982 | Vogel et al. ................ 422/56 |
| 4,356,149 | 10/1982 | Kitajima et al. . |
| 4,438,067 | 3/1984 | Siddiqi ...................... 422/56 |
| 4,557,900 | 12/1985 | Heitzmann .............. 422/56 X |

FOREIGN PATENT DOCUMENTS

| | | |
|---|---|---|
| 0013156 | 7/1980 | European Pat. Off. . |
| 0078040 | 5/1983 | European Pat. Off. . |
| 0078971 | 5/1983 | European Pat. Off. . |
| 2910134 | 9/1980 | Fed. Rep. of Germany . |
| 3222366 | 12/1982 | Fed. Rep. of Germany . |
| 3235658 | 4/1983 | Fed. Rep. of Germany . |
| 2950501 | 7/1983 | Fed. Rep. of Germany . |
| 2303290 | 10/1976 | France ..................... 436/169 |

*Primary Examiner*—Barry S. Richman
*Assistant Examiner*—Robert J. Hill, Jr.
*Attorney, Agent, or Firm*—Sprung Horn Kramer & Woods

[57] ABSTRACT

In a reagent strip for the dry-chemical detection of a component of an aqueous sample solution comprising a detection reagent in a membrane, the improvement wherein the membrane is an essentially anhydrous, but water-absorbing, membrane for a reagent substrate in an analytical agent for the dry-chemical detection of a component of an aqueous sample solution, comprising at least one hydrophobic film-forming, water insoluble organic polymer in which at least one hydrophilic organic polymer is dispersed as discrete particles. The reagent can be incorporated into the membrane when produced or can later be applied as by impregnation. The membrane performs as well as or better than multilayer strips.

12 Claims, No Drawings

WATER-ABSORBING, ESSENTIALLY WATER-FREE MEMBRANE FOR REAGENT SUBSTRATES AND METHODS OF PREPARING THE SAME

The invention relates to novel membranes and their use as reagent substrates for analytical agents which can be employed for the dry-chemical determination of components of aqueous solutions, mainly body fluids, such as blood, urine, serum, milk or the like, and their preparation from a water-in-oil emulsion of a hydrophilic water-containing, and preferably water-soluble, polymer and a solution of a hydrophobic, water-insoluble, film-forming polymer.

Compared with aqueous analytical methods, dry-chemical methods offer a number of advantages, which have led to a much wider use of test strips, especially in the diagnostic area. The advantages of dry analytical systems are, for example, the fact that they are simple to handle, so that even untrained persons can use them, the short analysis time, and the fact that no liquid reagents are required and there are therefore also no problems associated with the disposal of chemicals.

To carry out an analysis using test strips, the latter are dipped into the fluid to be investigated, such as, for example, urine, are removed, and after a certain time either the resulting coloration is assessed semiquantitatively by comparison with a color scale, or the intensity of the coloration is measured quantitatively by means of an optical apparatus; this can provide semiquantitative or quantitative information regarding the concentration of the component, of the aqueous fluid, which is to be analyzed. A frequently analyzed component of body fluids, such as blood or urine, is, for example, glucose.

If the fluid to be investigated consists of whole blood, the erythrocytes of the blood must be kept away from the reagent zone of the test strip or must be removed from the test strip after the blood sample has acted for a certain time, since otherwise the coloration formed during the detection reaction for the blood component to be determined cannot be assessed or measured.

A frequently used material for test strips is paper, which is impregnated with reagent solutions and employed directly or in conjunction with polymeric carrier materials or additional components, such as hydrophobic polymers or semipermeable membranes. Such test agents are described, for example, in U.S. Patent Specification Nos. 3,092,463 and 3,092,465, and EP-A 78 971. However, fibrous materials, such as paper, have serious disadvantages as reagent substrates in test strips. These disadvantages are described in detail in U.S. Patent Specification No. 4,042,335. Here, it is intended only to discuss the poorly reproducible analytical values, which are due to the non-uniformity of the paper material and at best permit a semiquantitative interpretation of the results.

Analytical results which can be evaluated quantitatively are obtained using test strips possessing synthetic reagent substrates which can be produced in standardized form. For example, according to U.S. Patent Specification No. 3,992,158 and DE-OS (German Published Specification) No. 3,222,366, such reagent substrates consist of hydrophilic polymers, such as gelatine or polyvinyl alcohol. However, reagent substrates of this type can only be employed in combination with other additional layers, as described in the abovementioned publications. The additional layers assume auxiliary functions which cannot be fulfilled by the hydrophilic reagent substrate alone. Examples of such additional auxiliary layers are spreading layers which distribute or spread a fluid sample so that it is possible to dispense with exact sample metering, or reflection layers which reflect light incident to the transparent base film and the reaction layer and thus permit measurement of the color intensity from the base site, without interference from cloudy or colored constituents of the fluid investigated. The cloudy or colored constituents, such as, for example, the erythrocytes in blood, must of course be prevented from passing through the reflection layer; for this purpose, it is necessary to employ a further layer as a barrier layer in certain circumstances.

Such multi-layer analytical systems are of course difficult to produce since a number of very different layers have to be brought into close contact with one another, for example by adhesion or lamination or by pouring liquid casting mixtures on top of one another. Because of the different hydrophilic or hydrophobic properties of the individual layers, poor adhesion may frequently be observed. Other disadvantages of multi-layer systems are described in detail, for example, in U.S. Patent Specification No. 4,356,149.

The reagent substrates consisting of gelatin or polyvinyl alcohol in such multi-layer test agents themselves have a number of disadvantages: they hinder, inter alia, the diffusion of reaction components, a fact which is referred to, for example, in DE-OS (German Published Specification) No. 3,222,366, and hence increase the time required for carrying out an analysis. Furthermore, hydrophobic and nigh molecular weight substances, in particular, diffuse only very slowly, if at all, and therefore also cannot be detected quantitatively, as is demonstrated in DE-OS (German Published Specification) No. 3,235,658.

Even reagent substrates consisting of hydrophobic polymers, such as ethylcellulose, cellulose acetate or polyisobutylene, which are used according to U.S. Patent Specification No. 3,630,957, have very small pores and therefore lead to long reaction times (described in German Patent Specification No. 2,950,501) and do not permit the detection of nigh molecular weight substances.

Higher reaction rates and hence shorter analysis times are achieved using porous reagent substrates. By means of capillary forces, the pores absorb some or all of the fluid applied and distribute it uniformly within the reagent substrate, so that the aqueous components rapidly come into contact with the reagents distributed in the reagent substrate. It is technically possible to adjust the pores so that, on the one hand, high molecular weight components of the aqueous sample are also able to penetrate, but on the other hand, troublesome, larger constituents, such as, for example, the erythrocytes of blood, remain on the surface of the layer and can be removed.

Such a porous or absorptive reagent layer is described in DE-OS (German Published Specification) No. 2,910,134. A water-tight film of polyvinyl propionate is rendered porous by the addition of solid, insoluble particles—referred to as film openers—consisting of, for example, titanium dioxide or cellulose, and can then serve as a reagent substrate for the detection of high molecular weight components of aqueous systems. The production of porous structures by the addition of pigments to polymer latices has long been known, and is reported, for example, in "Progress in Org. Coatings 11, 267-285 (1983)". The disadvantage of reagent layers of this type is the fact that the nature of the film opener has no effect on the course of the detection reaction which takes place in the pores or at the boundary with the hydrophobic polymer, that is to say tnere are few possibilities of variation for optimizing the reagent layer for particular detection systems.

The small range of variation also applies to the film-forming polymer, polyvinyl propionate being used exclusively as such in the examples of DE-OS (German Published Specification) No. 2,910,134.

Another porous analytical agent is described in EP-A 13 156. It is produced by adhesively bonding insoluble particles with an insoluble adhesive to form defined cavities which are intended to be suitable, in particular, for transporting large molecules, such as whole blood. This system has many disadvantages, which are described in detail in DE-OS (German Published Specification) No. 3,235,658. The particular disadvantage of this method is the fact that the three-dimensional structure is composed only of hydrophobic components, and aqueous liquid samples are therefore poorly held.

Hydrophilic, insoluble particles which contain color-forming reagents and are bonded to paper are used according to U.S. Patent Specification No. 3,993,451 as reagent substrates. Because of the powder form of the materials employeo, the particle size is difficult to monitor, and the color test is therefore prone to error. Uniform, hydrophilic, but water-insoluble, beads containing microvacuoles are claimed as reagent substrates in German Patent Specification No. 2,950,501. However, the process for their preparation is extremely complicated since the polymer has to be semipermeable, which is achieved only under very particular preparation conditions. The microvacuoles are produced by dispersing an aqueous reagent solution in a solution of cellulose triacetate in methylene chloride. In order to produce the beads, the resulting water-in-oil dispersion is in turn emulsified in a second water phase, a water-in-oil-in-water emulsion being formed. The water-insoluble beads are isolated from this by evaporating the organic solvent and filtering the residue, drying the product and fractionating according to size by screening with wire sieves. Beads of the desired size ($<100$ $\mu$m) are then adhesively bonded, as a monolayer or double layer, to a base film, the finished test strip only then being obtained. An advantage of this reagent substrate is in principle the fact that hydrophilic and hydrophobic reagents can be readily combined with one another since both an organic and an aqueous phase are present in the three-phase system during the preparation of the beads. However, a precondition is that the formation of the three-phase system, which is susceptible to problems, is not influenced by the reagents themselves, and the polymer formed remains semipermeable.

A simple combination of hydrophobic reagents with a hydrophilic binder layer is achieved according to U.S. Patent Specification Nos. 4,089,747 and 4,356,149 by distributing hydrophobic reagents as a solution in an organic solvent or as fine hydrophobic particles incorporated in a hydrophilic binder. These reagent layers are components of multi-layer analytical systems which have the disadvantages already discussed.

Another analytical unit which contains hydrophilic and hydrophobic components consists, according to DE-OS (German Puolished Specification) No. 3,235,658, of, inter alia, a core/shell polymer having a hydrophobic core and a hydrophilic shell. Such an analytical unit has a better retention capacity for hydrophobic or high molecular weight substances. Since the individual particles are connected to one another by adhesion of the hydrophilic outer layers, but the adhesion is reduced by the action of an aqueous sample, such layers are not resistant to wiping. For the analysis of whole blood, it is therefore necessary to apply an additional barrier layer onto the actual reagent layer in order to retain the erythrocytes, that is to say to construct a multilayer system with its known disadvantages.

A further component of multi-layer systems are layers which are described in U.S. Patent Specification No. 4,303,408 contain either a hydrophobic solvent dispersed in a hydrophilic phase, or an aqueous phase dispersed in a hydrqphobic phase. The object of the dispersed phase in the former case is to filter out hydrophobic components of the sample to be investigated, and in the latter case to filter out hydrophilic components, while the remaining solution can pass through unhindered. The dispersed aqueous phase contains, for example, complexing reagents, such as quaternary alkylammonium or phosphonium salts, which, in the form of side groups, may also be part of polymers. The filter action of the two-phase layers is intended to prevent the meeting of hydrophilic and hydrophobic reagents or sample components, which excludes their use as the sole reagent substrate.

EP-A 78 040 describes a film which consists of an organic, hydrophobic polymer and hydrophilic constituents, namely proteins, such as collagen or oligopeptides, and can serve as a closure for wounds. Although the film is permeable to vapor it is not permeable to liquid, and is therefore unsuitable as a reagent substrate for the analysis of aqueous liquids.

The overall requirements which an analytical agent for determining components of aqueous liquids has to meet are evident from the prior art described above. For greater clarity, these requirements are summarized briefly as follows:

1. Simple, reproducible production of the test agent.
2. All functions of customary test systems can be combined in one reagent layer, the ability to spread an aqueous sample, adequate resistance to wiping for wiping off erythrocytes when whole blood is used as the analytical fluid, and rapid penetration of the liquid sample being mentioned in particular.
3. The detection of high molecular weight and hydrophobic substances can be made possible by suitably modifying the reagent substrate.
4. Hydrophilic and hydrophobic reagents can be combined in a simple manner in one detection system.
5. The system offers a wide range of possibilities for variation, for optimization to specific analytical problems.

None of the large number of known analytical agents meets all these requirements adequately. It was therefore the object of the present invention to provide an analytical system which substantially meets these five requirements.

The object was achieved by combining one or more film-forming, water-insoluble, organic polymers with one or more water-containing, organic polymers and detection reagents, in one reagent substrate.

The invention relates to a water-absorbing, essentially water-free membrane for reagent substrates in analytical agents for the dry-chemical detection of components of aqueous sample solutions, which is characterized in that it comprises one or more hydrophobic, film-forming, water-insoluble organic polymers in which one or more hydrophilic, preferably water-soluble, organic polymers are distributed as a discontinuous phase.

Preferably, the hydrophilic polymers are contained in the pores of the membrane, the coherent phase of which consists of the film-forming, water-insoluble polymers.

The membranes according to the invention can be obtained by mixing a solution of one or more film-forming, water-insoluble organic polymers with a dispersion of one or more hydrophilic, water-containing polymers in an organic solvent, applying the mixture onto a base and drying it.

In another method for the preparation of the membranes according to the invention, the hydrophilic, water-containing polymer is dispersed in a solution of the film-forming, water-insoluble polymer in an organic solvent, and this dispersion, which corresponds to the above mixture in its composition, is applied onto a base and dried.

Hydrophilic organic polymers are understood here as meaning those polymers which absorb at least 20% by weight of water. Preferred polymers absorb 50% by weight of water, and particularly preferred polymers absorb more than 100% by weight of water. The most suitable polymers are water-soluble polymers which have a solubility of more than 1% by weight in water at room temperature. Such polymers are preferably dispersed in the organic solvent in the form of an aqueous solution.

Reagent substrates according to the invention consist of one of the membranes defined above, which contains one or more detection reagents (preferably all those required) for the determination of a component of the sample.

Analytical agents according to the invention for the dry-chemical detection of components of aqueous sample solutions are characterized in that they possess at least one of the reagent substrates according to the invention.

In the analytical method according to the invention, the agent according to the invention is brought into contact with the aqueous sample in a manner which is in itself known, and the resulting detection reaction (for example colour formation, fluorescence or luminescence) is monitored.

In the preparation of the reagent substrates according to the invention, the detection reagents are either dissolved in the mixture from which the membrane is prepared, or added in the form of a water-in-oil (W/O) dispersion or (less preferably) distributed in the membrane by subsequent impregnation of the latter. The organic solvents which may be used in this procedure should satisfy the criteria stated further below.

The preferably solid base for membrane production can consist of glass, metal or a synthetic or natural polymer which, when the mixture is applied and dried in order to produce the membrane or reagent substrate, is not completely dissolved or not surface-swollen to such an extent that it changes its external form. The base can be transparent or opaque. It preferably consists of polyethylene terephthalate, to which pigments can be added in order to render it in transparent to light, or of polyethylene-coated paper.

The membrane or the reagent substrate can also be produced on one of the abovementioned bases, detached from this, and applied, by means of a suitable adhesive, onto another base, which in this case can also consist of a material, such as polycarbonate, cellulose acetate, polystyrene etc., which is soluble in customary organic solvents.

Suitable film-forming, water-insoluble organic polymers are those which absorb less than 1% by weight of water by swelling, which have a solubility of more than 1% by weight in one of the organic solvents described further below, and which give a film after the solvent has been evaporated. The polymers can be, for example, polymers of ethylenically unsaturated monomers, polyaddition or polycondensation products, or natural products or derivatives of these. Soluble polyhydrocarbons, polydienes, polyvinyl compounds, polyacrylates or -methacrylates, polycarbonates, polyacetals, polyethers, polyurethanes, phenol resins, polyesters, polysulphones, polyamides and polyimides and organo-soluble polysaccharides and derivatives of these are preferably used.

Particularly preferred among these are: bisphenol A polycarbonate, polystyrene, poly-p-methylstyrene, polytrifluoromethylstyrenes, polymethyl methacrylate, cellulose acetate, cellulose acetobutyrate, cellulose acetopropionate, styrene/acrylonitrile copolymers, styrene/maleic anhydride copolymers, methyl methacrylate/methyl acrylate copolymers, aromatic polyesters, tetramethylbisphenol A polycarbonate, polyvinyl acetate, polyisobutylene, copolymers of styrene and butadiene or isoprene and copolymers of acrylonitrile and butadiene, the monomer building of which in each case can be arranged randomly or blockwise, and ethylcellulose.

Of course, it is also possible to use mixtures of the abovementioned polymers, or copolymers having a random or blockwise distribution of the monomer units.

In the preparation process according to the invention, the film-forming, water-insoluble polymer is present as a solution in an organic solvent, preferably in a concentration range between 1 and 30% by weight. A concentration between 5 and 15% by weight is particularly preferred. The solvent can be identical to that of the organic phase of the dispersion of the water-soluble polymer, or different from this. In both cases, the organic solvents used should (a) have a miscibility gap with water;
(b) not extract the hydrophilic polymer from the aqueous phase; and
(c) have boiling oints below 150° C., preferably below 120° C., particularly preferably below 100° C.

Suitable solvents for a predetermined combination of hydrophilic and hydrophobic polymers can be determined by means of simple preliminary experiments.

Examples of solvents which can be used are ethers, such as diethyl ether, dipropyl ether or diisobutyl ether, ketones, such as ethyl methyl ketone, diethyl ketone or methyl isobutyl ketone, esters, such as ethyl acetate, butyl acetate or diethyl carbonate, higher alcohols, such as butanol, pentanol, hexanol or cyclohexanol, aliphatic and aromatic hydrocarbons, such as hexane, paraffin mixtures, cyclohexane, toluene or xylene, and halogenated hydrocarbons, such as trichloroethylene, chloroform, carbon tetrachloride, perchloroethylene, methylene chloride or chlorobenzene, as well as mixtures of the stated solvents or similar solvents.

Aliphatic or aromatic hydrocarbons which may or may not be halogenated, or mixtures of these, are preferably used. Hexane, cyclohexane, paraffin mixtures, such as ®Isopar M, toluene, trichloroethylene, chloroform, perchloroethylene and methylene chloride may be mentioned.

The hydrophilic polymers which are employed according to the invention can be of natural or synthetic origin and ionic or non-ionic. For example, starch, gelatine or derivatives thereof, agar-agar, pullulanes, hydrophilic cellulose derivatives and hydrophilic polymers and copolymers can be used. Among these, the following may be mentioned: polyethyleneimine, polyacrylic and methacrylic derivatives, such as polyacrylamide, poly-N-methyl- or N,N-dimethylacrylamide, polyvinyl alcohol, polyacrylic acid and salts thereof, polyalkylaminoalkyl methacrylates or -amides and salts of these, polystyrenesulphonic acid and salts thereof, polyacrylamido-2-methyl-2-propanesulphonic acid and salts thereof, polyvinylimidazole, poly-N-vinyllactams, such as poly-N-vinylpyrrolidone or polyvinylcaprolactam, poly-N-vinylamides, such as poly-N-vinyl-N-methylacetamide, poly-N-vinylurethanes, copolymers with malic anhydride and copolymers which contain basic building blocks of the above polymers distributed randomly or blockwise.

The hydrophilic polymers are preferably dispersed in the organic phase with the addition of a detergent as an emulsifier, which can be chosen from Mc'Cutcheons Annual 1971 in accordance with the combination of the hydrophilic and hydrophobic phase, the criteria which apply to the organic phase being the same as those for the organic solvent for the preparation of the solution of the water-insoluble, film-forming polymer. ®Span, ®Tween and ®Triton grades, ®Pluronics and Na dodecylbenzenesulphonate may be mentioned as examples of possible detergents. The weight of the detergents is between 0 and 50%, preferably between 1 and 30%, relative to the organic phase.

The amount of the detergents shoud be chosen so that a fine dispersion having sufficient stability for the duration of the process for the preparation of the membrane is formed.

The organic phase or the organic solvent in which the hydrophilic polymers are dispersed can in favorable cases already contain the film-forming, water-insoluble polymer, so that the process step of mixing the w/o dispersion of the hydrophilic polymer with the solution of the film-forming polymer is dispensed with.

The hydrophilic polymers which are dispersed in the organic solvent can contain different amounts of water, but should contain at least 20% by weight. Depending on the type of polymer, the water content can be substantially higher and, in the case of water-insoluble, but water-swellable, types, can be varied over the entire range up to maximum swelling at room temperature. Water-soluble polymers are used as an aqueous solution, in a concentration greater than one percent. The water content of the hydrophilic polymers is preferably between 50 and 5,000% by weight, relative to the hydrophilic polymer. A range between 100 and 2,000% by weight is particularly preferred. In this context, it should be noted that a water content of, for example, 200% by weight can be achieved both by swelling (water absorption) of an insoluble polymer and by water absorption by a water-soluble polymer, the latter case also being referred to as a highly concentrated solution of the polymer in water. The water absorption capacity is restricted in the case of insoluble polymers by the maximum degree of swelling, which depends on the chemical nature and in particular on the crosslinking. Water contents of above 100% by weight can be achieved in every case with water-soluble polymers.

To effect water absorption, the required amount of water is added to the hydrophilic polymers, and, if necessary, the latter are mechanically comminuted in order to achieve fine dispersion during the subsequent dispersing in the organic solvent. In the case of insoluble polymers, it is advantageous if they are present in the form of fine particles even before the swelling process. Aqueous solutions having a low viscosity can be finely dispersed by combining the aqueous polymer solution and the organic phase by pouring, and shaking the mixture vigorously. Aids to dispersing, such as, for example, ultra-high speed stirrers, ultrasound or special mixing nozzles which are operated under high pressures are advantageous especially for dispersing viscous solutions, gels or swollen particles. The volume ratio of the hydrophilic phase to the organic phase should be chosen so that the dispersing process takes place in an optimum manner; for this purpose, the mixture must have a certain viscosity, depending on the dispersing method. This viscosity can be increased by dissolving organic polymers in the organic solvent.

Preferred volume ratios of the hydrophilic phase to the organic phase are between 1:100 and 2:1, and particularly preferred ratios are between 1:25 and 1.5:1. A volume ratio between 1:10 and 1:1 is very particularly preferred.

After the dispersing process, the dispersion can be diluted or concentrated again in order to match its viscosity to, for example, the viscosity of the solution of the hydrophobic polymer in an organic solvent, with which solution the dispersion is mixed in order to produce the membrane. This mixing process can be carried out either by vigorous shaking or with the aid of mechanical apparatuses, such as stirrers, mixing nozzles, etc. For predetermined concentrations of the two phases, the volume ratio of the W/O dispersion of the hydrophilic, water-containing polymers to the solution of the water-insoluble, film-forming polymer depends on the amounts of hydrophilic and water-insoluble, film-forming polymers which are required for functioning of the membrane and are described further below. If a certain volume ratio is prescribed for technical reasons, the ratio of the amounts of film-forming and hydrophilic polymers in the membrane must be set via their concentrations in the phases used for membrane production.

Dispersing of the hydrophilic, water-containing polymers in the organic solvent can, like the mixing of this dispersion with the solution of the film-forming, water-insoluble polymer, be carried out at any temperature between the solidification and boiling points of the solvents used. Preferred temperatures are between 0° and 100° C. Room temperature is particularly preferred.

To produce the membrane, the mixture described above is applied onto a substrate, and this can be achieved by painting, spraying, applying with a knife-coater or casting. Uniform thicknesses can best be applied using appropriate mechanical apparatuses which are familiar to the skilled worker. Since the viscosity of the mixture can be varied within wide limits, optimum casting behavior can be established for any casting technique. The thickness of the freshly applied layer is preferably between 10 μm and 1,000 μm and depends on the solids content of the mixture and the desired thickness of the finished membrane. This is obtained by drying the mixture applied on the substrate. Drying can be accelerated by blowing on heated air, by heating or by applying a vacuum. In certain circumstances, low-boiling solvents evaporate sufficiently rapidly at room temperature even without additional measures.

In a preferred embodiment of the drying procedure, this procedure is carried out using air having a high relative humidity. Suitable atmospheric humidities are between 20 and 100% relative humidity, preferably between 40 and 100%. The best results are obtained by drying with air of 60–95% relative humidity.

Drying may also be carried out in a plurality of stages, drying in the 1st stage advantageously being carried out using air which has a high moisture content. In the subsequent stages, it is possible to use air having lower moisture contents and, for example, higher temperatures. The final drying stage should be carried out using heated air (temperature between 20° and 80° C., preferably between 30° and 60° C.) which has a low moisture content, if complete drying of the membrane is desired.

In a preferred embodiment of the invention, the dispersion of the hydrophilic, water-containing polymer in the organic solvent (oil phase) is prepared by inverse emulsion polyerization (water-in-oil) of an aqueous solution of monomers or monomer mixtures which is dispersed in the oil phase. The inverse emulsion polymerization process is known, and is described, for example, in U.S. Patent Specification Nos. 3,284,393 and 3,691,124, DE-OS (German Published Specification) Nos. 1,745,176, 2,432,699 and 2,926,103, EP-A 68 955 and British Patent Specification No. 1,482,515. Emulsifiers, polymeric stabilizers, initiators, oil phases and possible monomers and monomer combinations which can advantageously be employed are also listed there. W/O dispersions which are particularly suitable for the preparation of the membranes or reagent substrates according to the invention are obtained in inverse emulsion polymerization of the following neutral, basic or acidic monomers, or combinations thereof: acrylamide, methacrylamide, N,N-dimethylacrylamide, N-vinylpyrrolidone, N-vinylcaprolactam, N-vinyl-N-methylacetamide, N-vinylacetamide, N-vinylurethanes; acrylic acid, methacrylic acid, styrenesulphonic acid, acrylamido-2-methyl-2-propanesulphonic acid and salts of these, N-vinylimidazole, dimethylaminoethyl methacrylate and -methacrylamide, dimethylaminopropyl methacrylate and -methacrylamide, and salts thereof, as well as mixtures of these monomers. Very particularly preferred monomers are acrylamide and mixtures of the stated monomers with acrylamide.

Suitable initiators which initiate the polymerization of the monomers are all free radical formers, $uch as, for example, peroxo or azo compounds. Photoactivated initiator systems can also be employed. The initiators are advantageously chosen from the group comprising the azo compounds since, for example, residues of incompletely consumed peroxide initiators can react with sensitive detection reagents which are added to the reagent substrate during the preparation of the latter.

The aqueous phase of the W/O dispersion can contain additives, such as salts, thickeners or molecular weight regulators. It is also possible for substances which, for example, improve the stability of the dispersion, increase the viscosity or affect the surface tension to be added to the organic phase of the dispersion before or after the polymerization, or for the dispersion to be diluted, concentrated or partially dewatered after its preparation. Preferably, the W/O dispersion contains polymeric stabilizers, which are listed, for example, in U.S. Patent Specification Nos. 3,691,124, 3,979,349 and 3,948,866 or British Patent Specification 1,482,515.

If required, different W/O dispersions can be mixed in order to combine, for example, dispersions possessing different particle sizes or containing different hydrophilic polymers which differ in type or in mean molecular weight. Furthermore, water-soluble polymers can be crosslinked by reaction with suitable reagents after preparation of the W/O dispersion.

In the preparation of the membranes or reagent substrates according to the invention, various property-modifying additives can be introduced into the mixture of the solution of the film-forming, water-insoluble organic polymers and the dispersion of the hydrophilic, water-containing polymers. To increase the reflection, pigments, such as titanium dioxide, silica gel and the like, can be dispersed in the casting mixture. Other possible additives are thickeners for increasing the viscosity, or compounds which are suitable for improving the adhesion of the reagent substrate to the base when the reagent substrate remains on the base, or to reduce the said adhesion when the reagent substrate is to be detached from the base. With the aid of surface-active substances or wetting agents, it is possible to modify the surface properties of the reagent substrate in order, for example, to improve wetting by the sample material or to increase the brilliance of the reaction color. The properties of the reagent substrate are also affected by plasticizers, for example the hardness and strength, the adhesion, etc.

Although a substantial advantage of the reagent substrate according to the invention is the fact that just one layer fulfils all functions of a diagnostic agent for determining components of aqueous systems, the reagent substrates according to the invention can also be used for constructing multi-layer analytical elements in order, for example, to effect spatial separation of incompatible reaction components which would otherwise react with one another at as early a stage as the preparation of the reagent substrate, or to influence the stepwise course of a reaction sequence by creating optimum conditions (for example different pH values) in different reagent substrates for each reaction stage. A second reagent substrate which is superimposed on the actual reagent substrate which contains the detection reagents for a particular substance can also fulfil the task of removing compounds which interfere with the detection reaction, that is to say, of not letting them pass through or of rendering them harmless. This can be achieved by physical or chemical methods. One or more reagent-free cover layers can serve as filter layers, spreading layers or reflection layers. To obtain thicker layers, several reagent substrates which contain the same reagents can be cast one on top of the other.

The reagent substrates according to the invention can also be combined with layers which are known per se and are used for analytical test agents, such as, for example, gelatine, polyvinyl alcohol, etc. In the case of combination with hydrophilic layers, reagents can be particularly readily kept apart from one another since, especially during the process for the preparation of the multilayers by successive casting processes, no mixing of the hydrophilic and hydrophobic casting mixtures or layers takes place.

To carry out an analysis using the reagent substrates according to the invention, a test strip which contains at least one reagent substrate with suitable detection reagents, for example for a glucose determination, and a base film is dipped into the fluid to be investigated, for example urine, and is removed, and the resulting coloration is evaluated visually or spectroscopically. If the fluid to be investigated consists of whole blood, a drop of this is applied onto a reagent substrate, a short time is allowed to elapse, and excess fluid, including the erythrocytes, is simply wiped off. The resulting coloration can then be evaluated. The drop size has no effect on the color intensity, so that the sample volume need not be metered exactly.

The amount of fluid sample which is absorbed by the reagent substrate depends not only on the nature of the hydrophobic, film-forming polymers and the hydrophilic polymers and any additives, for example for surface modification, but also on the ratio of the amounts of hydrophobic, film-forming polymers and the hydrophilic polymers. This ratio also effects the resistance of the reagent substrate to wiping. While highly water-absorptive layers which are not resistant to wiping are formed in the case of large amounts of hydrophilic polymers, very large amounts of hydrophobic, film-forming polymers lead to resistant films which absorb only small amounts of aqueous liquid. Depending on the intended use, the properties of the reagent substrate can thus be adjusted. For the analysis of whole blood, the reagent substrate must, for example, be resistant to wiping in order to be able to remove the erythrocytes, whereas for urine analysis resistance to wiping is not necessary. For the latter case, relatively high hydrophilicity of the reagent substrate may be advantageous for retaining a sufficiently large amount of liquid when the test strip is dipped into the urine sample for a short time. Advantageously, the weight ratio of the amounts of hydrophobic, film-forming polymers to hydrophilic, water-containing polymers in the reagent substrates is between 1:10 and 10:1. Preferably, this ratio is between 1:5 and 5:1. A ratio between 1:2 and 2:1 is very particularly preferred.

The examples which follow serve to illustrate the present invention in more detail.

In Examples 1-16, the preparation of W/O dispersions of water-soluble polymers by dispersion polymerization is described. Such dispersions are preferably used for the preparation of the reagent substrates according to the invention.

EXAMPLE 1

In a 1 face-ground vessel equipped with a paddle stirrer, 440 g of chloroform, 12 g of ®Span 80 (R Span 80 is a sorbitan monooleate), 4 g of a copolymer of stearyl methacrylate and acrylamide (proportions by weight 82.6/17.4) and 0.2 g of azo-bis-(isobutyronitrile) are initially taken, degassed and heated to 50° C. At this temperature, 20% of a degassed solution of 40 g of acrylamide and 80 g of $H_2O$ is rapidly added dropwise under a gentle stream of nitrogen. The remainder of the monomer solution is added dropwise in the course of 2 hours. When the addition is complete, stirring is continued for 2 hours. The dispersion contains 6.9% by weight of polyacrylamide.

EXAMPLE 2-16

W/O dispersions with components or reaction conditions, where these differ from the data in Example 1, are listed in Table 1 and are prepared analogously to Example 1.

TABLE 1

| Example No. | Organic phase | Emulsifier (weight/%+) | Monomers (weight/%) | $H_2O$ content++ | T °C. |
|---|---|---|---|---|---|
| 2 | trichloreoethylene | Span 80 (2.6) | acrylamide (6.9) | 66.7 | 60 |
| 3 | " | Span 60 (2.6) | acrylamide (6.9) | 60 | 70 |
| 4 | toulene | Span 80 (4.3) | acrylamide (8.2) | 66.7 | 55 |
| 5++++ | cyclohexane | Span 60 (10.0) | acrylamide (11.2) | 60 | 80 |
| 6 | chloroform | Span 80 (3.5) | acrylamide (6.9) | 80 | 50 |
| 7+++ | " | Span 80 (3.5) | acrylamide (6.9) | 66.7 | 55 |
| 8 | " | Span 80 (2.6) | acrylamide (13.2) | 66.7 | 55 |
| 9++++ | " | Span 80 (2.6) | acrylamide (6.9) | 66.7 | 55 |
| 10 | " | " | N,N—dimethylacrylamide (6.9) | " | " |
| 11 | " | " | N,N—dimethylaminoethyl methacrylate.HCl/acrylamide (1.7/5.2) | " | " |
| 12 | " | " | Na acrylate/acrylamide (4.0/3.4) | " | " |
| 13 | " | " | N—vinylpyrrolidone/acrylamide (3.4/3.4) | " | " |
| 14 | " | " | methacrylamide (6.9) | " | " |
| 15 | " | " | N—vinylacetamide/acrylamide (3.5/3.5) | " | " |
| 16 | " | " | N—vinylimidazole/acrylamide (3.5/3.5) | " | " |

+relative to organic phase
++relative to aqueous phase
+++without the addition of stearyl methacrylate/acrylamide copolymer
++++with 0.5 g of azo-bis(isobutyronitrile)

Example 17 describes the simple preparation of a reagent substrate, according to the invention, which contains detection reagents for glucose determination.

EXAMPLE 17

6 mg of glucose oxidase (150 U/mg) and 6 mg of peroxidase (80 U/mg) are dissolved in 0.2 ml of 1M citrate buffer solution (pH 5.5).

This solution is dispersed in the form of fine droplets in 0.4 ml of chloroform which contains 40 mg of dodecylbenzenesulphonate, by shaking. The dispersion formed is added to a mixture of 2.5 ml of the dispersion from Example 1, 2.5 ml of a 7.5% strength solution of a polycarbonate (prepared by continuous phase-boundary polycondensation; $\eta_{rel}=1.30$, measured in 0.5% strength solution in methylene chloride) in chloroform, and 0.1 g of tetramethylbenzidine. The mixture is shaken vigorously, and applied onto a polyester film with a knife-coater (wet layer 250 μm). The finished reagent film is obtained after drying for a short time at room temperature.

To determine the glucose concentration of whole blood, a drop of blood is applied onto the reagent film and wiped off after 15 sec. After 1 minute, the detection reaction is complete, and the glucose concentration of the blood sample can be determined from the color intensity of the test zone. For glucose concentrations in the range between 0 and 500 mg/dl, increasing color intensities of the test zone, proportional to the concentration of the sample solution, are observed. The color intensity is not dependent on the volume of sample applied. When transparent polyester &ilms are used as a base, the coloration can be observed both from above and from below.

To determine glucose in urine, the dry reagent film is cut into narrow strips, which are dipped for a short time into urine samples having different glucose contents. The color reaction is complete after about 1 minute. Blue colorations which are well graded in their intensity are obtained in the range between 0 and 500 mg/dl, depending on the glucose concentration.

The ingredients of other aqueous liquids can also be determined in a manner analogous to that demonstrated for the detection of substances for analysis in whole blood and urine.

In the examples below, glucose test films are prepared analogously to Example 17, using the dispersions and hydrophobic polymers listed in Table 2.

TABLE 2

| Example No. | Dispersion from Example No. (ml) | Polymer | Solvent | Volume of polymer solution (ml) |
|---|---|---|---|---|
| 18 | 6 (2.5) | 1 | CHCl₃ | 2.5 |
| 19 | 7 (2.5) | 2 | CHCl₃ | 2.5 |
| 20 | 9 (2.5) | 3 | CHCl₃ | 2.5 |
| 21 | 9 (2.5) | 4 | CHCl₃ | 2.5 |
| 22 | 6 (2.5) | 5 | CHCl₃ | 2.5 |
| 23 | 8 (1.3) | 6 | CHCl₃ | 3.7+ |
| 24 | 8 (2) | 7 | CHCl₃ | 3 |
| 25 | 8 (2) | 8 | CHCl₃ | 3 |
| 26 | 8 (2) | 9 | CH₂Cl₂ | 3 |
| 27 | 5 (2.5) | 10 | Cyclohexane | 2.5 |
| 28 | 9 (2.5) | 11 | CHCl₃ | 2.5 |
| 29 | 4 (2) | 12 | Toluol | 3 |
| 30 | 8 (1.7) | 12 | CHCl₃ | 3.3 |
| 40 | 9 (2.5) | 13 | CHCl₃ | 2.5 |
| 41 | 2 (2.5) | 14 | CHCl₃ | 2.5 |
| 42 | 3 (2.5) | 15 | CHCl₃ | 2.5 |
| 43 | 13 (2.5) | 16 | CHCl₃ | 2.5 |
| 44 | 10 (2.5) | 17 | CHCl₃ | 2.5 |
| 45 | 8 (2) | 18 | CHCl₃ | 3 |
| 46 | 11 (2.5) | 17 | CHCl₃ | 2.5 |
| 47 | 12 (2.5) | 17 | CHCl₃ | 2.5 |
| 48 | 14 (2.5) | 17 | CHCl₃ | 2.5 |
| 49 | 15 (2.5) | 17 | CHCl₃ | 2.5 |
| 50 | 16 (2.5) | 17 | CHCl₃ | 2.5 |
| 51 | 6 (2.5) | 19 | CHCl₃ | 2.5 |

[30] 5% strength solution

Chemical composition of the hydrophobic polymers used:

1. Copolymer of 80% of styrene and 20% of acrylonitrile;
2. Polymethyl methacrylate; [η] (25° C., tetrahydrofuran) = 0.6
3. Copolymer of 80% of styrene and 20% of maleic anhydride;
4. Copolymer of 75% of styrene, 15% of acrylonitrile and 10% of maleic anhydride;
5. Copolymer of 56% of styrene, 28% of methyl methacrylate and 16% of maleic anhydride;
6. Cellulose acetate; $\eta_{rel}$ (20% strength in acetone:ethanol = 9:1) = 180
7. Cellulose acetobutyrate; $\eta_{rel}$ (20% strength in acetone:ethanol = 9:1) = 200
8. Cellulose acetopropionate; $\eta_{rel}$ (20% strength in acetone:ethanol = 9:1) = 200
9. Polycarbonate obtained from tetramethylbisphenol A; $\eta_{rel}$ (measured on a 0.5% strength solution in methylene chloride) = 1.33
10. Polyisobutylene; (ᴿOppanol B 100)
11. Polyester obtained from tetramethyl-bisphenol A and terephthalic acid; $\eta_{rel}$ (measured on a 0.5% strength solution in methylene chloride) = 1.4
12. Polystyrene; [η] = 0.9 (toluene, 25° C.)
13. Polyvinyl acetate; molecular weight: 37,000 g/mol
14. Polycarbonate of bisphenol A; $\eta_{rel}$, measured on a 0.5% strength solution in methylene chloride = 1.28
15. Polycarbonate of bisphenol A; $\eta_{rel}$ (0.5% strength in methylene chloride) = 1.29
16. Polycarbonate of bisphenol A, with 0.5 mol % of isatin-biscresol as branching agent; $\eta_{rel}$ (0.5% strength in methylene chloride) = 1.32
17. Polycarbonate of bisphenol A; $\eta_{rel}$, measured on a 0.5% strength solution in methylene chloride = 1.30
18. Poly-p-methylstyrene; [η] = 0.8 (toluene, 25° C.)
19. SBS 3-block copolymer consisting of 30% of styrene and 70% of butadiene, prepared by anionic polymerisation in hexane using butyl-lithium as an initiator, molecular weight: 150,000 g/mol.

After test solutions have been applied, each of the glucose test files from Examples 18–51 exhibits good wipeability and color intensities which increase in proportion to the concentration of glucose in the test solutions.

Example 52 below illustrates the effect of the ratio of the amounts of hydrophilic polymer to hydrophobic polymer on the properties of the reagent substrate according to the invention.

EXAMPLE 52

The dispersion from Example 8 was used to prepare glucose test films according to Example 17, various weight ratios of polyacrylamide to polycarbonate being seet by varying the amounts of dispersion and polycarbonate solution.

| Weight ratio polyacrylamide/polycarbonate | Film properties |
|---|---|
| 5:1 | irregular film, dissolves with water |
| 2:1 | smooth film, good resistance to wiping, uniform coloration; from 2:1 to 1:2, the water absorption decreases and the resistance to wiping increases. |
| 1:1 | |
| 1:2 | |
| 1:5 | Film becomes colored in a non-uniform manner; color is removed when the sample solution is wiped off. |

The suitability of the reagent substrates according to the invention for the detection of high molecular weight compounds is shown in Example 53 by preparing a test film for glucose oxidase.

EXAMPLE 53

15 mg of peroxidase (80 U/mg) and 50 mg of glucose are dissolved in 0.5 ml of citrate buffer solution (1M, pH 5.5).

This solution is dispersed in a solution of 0.1 g of dodecylbenzenesulphonate paste (75% strength), 0.1 g of tetramethylbenzidine and 0.1 g of polymer 15 (from Example 42) in 1.0 ml of chloroform.

0.2 ml of this dispersion is added to a mixture of 2.5 ml of the dispersion from Example 1 and 2.5 ml of a 7.5% strength solution of polymer 15 in chloroform, and the mixture is mixed thoroughly. The mixture is applied as a film onto a polyester film by means of a knife-coater (wet layer 250 μm), and is dried at room temperature.

After glucose oxidase solutions of various concentrations have been applied to the reagent film and the solutions have been wiped off after 1 minute, it is possible, after a further minute, for the values of the reflected intensities of the test zone to be determined quantitatively in a reflection photometer, these values corresponding to the concentrations.

The suitability of the reagent substrates according to the invention for the detection of further substances for analysis is demonstrated in Examples 54–55.

EXAMPLE 54

A test film for potassium ions is prepared by mixing 2.5 ml of the dispersion from Example 1 and 0.2 ml of 2-nitrophenyl butyl ether with a solution of 3.5 mg of Gibbs reagent (7-(n-decyl)-2-methyl-4-(3',5'-dichloroquinone-4-imido)-1-naphthol), 9.0 mg of crown ether (2,3 naphtho-15-crown-5) and 2.5 ml of a 7.5% strength solution of polymer 17 in chloroform, and applying the mixture onto a polyester film in a layer thickness of 200 μm. The dry film gives blue colorations of different intensities with potassium chloride solution of different concentrations (between 0 and 9 mmol/l).

EXAMPLE 55

To prepare a reagent film for the detection of acetoacetate, a solution of 12.3 g of $MgSO_4$ and 1.3 g of $Na_2Fe(CN)_5NO.2H_2O$ in 15 ml of water is adjusted to pH 9–10 by means of 45% strength sodium hydroxide solution.

12 ml of this solution are dispersed in 32 ml of a 7.5% strength solution of polymer 17 in chloroform, which solution contains 2.3 g of dodecylbenzenesulphonate paste (75% strength). 2.5 ml of this dispersion are mixed with 2.5 ml of the dispersion from Example 1, and the mixture is applied onto polyethylene-coated paper by means of a knife-coater (250 μm).

After drying at room temperature has been carried out, tests with acetoacetate solutions give red colorations which exhibit good gradation in their intensity, according to the concentrations of the solutions.

EXAMPLE 56

Preparation of a glucose test strip 60 ml of a solution of cellulose acetobutyrate (polymer 7 in Table 2) in chloroform (7.5% strength), which solution contains 1 g of tetramethylbenzidine and 1.2 g of sodium dodecylbenzenesulphonate, are shaken vigorously with 30 ml of a 6.8% strength solution of polyvinylpyrrolidone (molecular weight 400,000 g/mol) in 0.1M citrate buffer (pH 5.5), and the mixture is forced under a pressure of 9 bar through a nozzle (φ of the hole 0.3 mm). This gives a finely divided dispersion. 50 ml of this dispersion are mixed with a dispersion of a solution of 11 mg of glucose oxidase (200 U/mg) and 60 mg of peroxidase (80 U/mg) in 2 ml of citrate buffer (1M, pH 5.5) dispersed in 4 ml of chloroform which contains 0.4 g of sodium dodecylbenzenesulphonate, and the mixture is cast (180 μm wet layer) onto a polyester film by means of a slot die (1.8 cm wide). Drying is effected by blowing with air: 10 minutes with air at 25° C. and 90% relative humidity and then 10 minutes with air at 40° C. and 20% relative humidity.

The finished test film is bonded to a white base film and cut into 0.5 cm wide strips. The strips are tested with whole blood samples having glucose contents between 20 and 400 mg/dl (duration of action before being wiped off: 15 sec). The detection reaction is complete after 1 minute in each case. The color intensity of the test field increases uniformly with increasing glucose concentration of the blood samples.

It will be understood that the specification and examples are illustrative but not limitative of the present invention and that other embodiments within the spirit and scope of the invention will suggest themselves to those skilled in the art.

What is claimed is:

1. An essentially anhydrous, but water-absorbing, membrane for a reagent substrate in an analytical agent for the dry-chemical detection of a component of an aqueous sample solution, comprising at least one hydrophobic film-forming, water-insoluble organic polymer selected from the group consisting of polyhydrocarbons, polydienes, polyvinyl compounds, polyacrylates or -methacrylates, polycarbonates, polyacetals, polyethers, polyurethanes, phenol resins, polyesters, polysulphones, polyamides and polyimides and organo-soluble polysaccharides in which at least one hydrophilic organic polymer capable of absorbing at least 20% by weight of water is dispersed as discrete particles.

2. The membrane according to claim 1, wherein the at least one hydrophilic polymer is contained in pores of a coherent phase of the membrane made up of the at least one hydrophobic, water-insoluble polymer.

3. The membrane according to claim 1, wherein the weight ratio of the at least one hydrophilic polymer to the at least one hydrophobic polymer is between 10:1 and 1:10.

4. A process for producing an essentially anhydrous, but water-absorbing, membrane for a reagent substrate in an analytical agent for the dry-chemical detection of a component of an aqueous sample solution, comprising mixing a solution of at least one film-forming, hydrophobic water-insoluble organic polymer selected from the group consisting of polyhydrocarbons, polydienes, polyvinyl compounds, polyacrylates or -methacrylates, polycarbonates, polyacetals, polyethers, polyurethanes, phenol resins, polyesters, polysulphones, polyamides and polyimides and organo-soluble polysaccharides with a dispersion of at least one hydrophilic, water-containing organic polymer, wherein the hydrophilic polymer is capable of absorbing at least 20% by weight of water, in an organic solvent to form a mixture, applying the mixture onto a base, and drying.

5. A process for producing an essentially anhydrous, but water-absorbing, membrane for a reagent substrate in an analytical agent for the dry-chemical detection of a component of an aqueous sample solution, comprising dispersing at least one hydrophilic, water-containing, organic polymer, wherein the hydrophilic polymer is capable of absorbing at least 20% by weight of water, in a solution of at least one film-forming, hydrophobic, water-insoluble organic polymer selected from the group consisting of polyhydrocarbons, polydienes, polyvinyl compounds, polyacrylates or -methacrylates, polycarbonates, polyacetals, polyethers, polyurethanes, phenol resins, polyesters, polysulphones, polyamides and polyimides and organo-soluble polysaccharides to form a dispersion, applying the dispersion onto a base, and drying.

6. In a reagent strip for the dry-chemical detection of a component of an aqueous sample solution comprising a detection reagent in a membrane, the improvement wherein the membrane is a membrane according to claim 1.

7. The reagent strip according to claim 6, further including a substrate and at least one additional layer.

8. A process for preparing a reagent strip which includes a detection reagent in a membrane comprising mixing a solution of at least one film-forming, water-insoluble organic polymer selected from the group consisting of polyhydrocarbons, polydienes, polyvinyl compounds, polyacrylates or -methacrylates, polycarbonates, polyacetals, polyethers, polyurethanes, phenol resins, polyesters, polysulphones, polyamides and polyimides and organo-soluble polysaccharides with at least one hydrophilic organic polymer which contains at least 20% by weight of water to form a mixture, with the solution of the at least one water-insoluble polymer or the at least one hydrophilic polymer or both being pre-mixed with a reagent, applying the mixture onto a base, and drying.

9. The process according to claim 8, wherein the reagent is hydrophobic and is pre-dissolved in the solution of the at least one water-insoluble polymer.

10. The process according to claim 8, wherein the at least one hydrophilic polymer is initially present in a water-in-oil emulsion.

11. The process according to claim 10, wherein the reagent is hydrophilic and is present in the aqueous phase of the water-in-oil emulsion.

12. The process according to claim 10, wherein the water-in-oil dispersion of the at least one hydrophilic, water-containing polymer is prepared by inverse emulsion polymerisation of water-soluble monomers.

* * * * *

UNITED STATES PATENT AND TRADEMARK OFFICE
CERTIFICATE OF CORRECTION

PATENT NO.   : 4,780,411
DATED        : Oct. 25, 1988
INVENTOR(S)  : Piejko et al.

It is certified that error appears in the above-identified patent and that said Letters Patent is hereby corrected as shown below:

| | |
|---|---|
| Col. 2, line 32 | Correct spelling of --high-- |
| Col. 3, line 5 | Correct spelling of --there-- |
| Col. 3, line 27 | Correct spelling of --employed-- |
| Col. 4, line 14 | Insert --and-- before "contain" |
| Col. 7, line 21 | Correct spelling of --maleic-- |
| Col. 9, line 52 | Correct spelling of --such-- |
| Col. 11, Example No. 5 | Delete last "+" |
| Col. 13, line 6 | Correct spelling of --films-- |
| Col. 13, line 48 | Delete "30" and substitute --+-- |

Signed and Sealed this

Third Day of October, 1989

Attest:

DONALD J. QUIGG

*Attesting Officer*    Commissioner of Patents and Trademarks